United States Patent [19]

Fukuda et al.

[11] Patent Number: 4,748,273

[45] Date of Patent: May 31, 1988

[54] AMPHIPHILIC DIACETYLENE COMPOUND CONTAINING BENZENE RING AND FILM PREPARED THEREFROM

[75] Inventors: Kiyoshige Fukuda, Tokyo; Yasunori Yoshioka, Ashiya; Masakazu Uekita, Kobe, all of Japan

[73] Assignee: Kanegafushi Kagaku Kogyo Kabushiki Kaisha, Osaka, Japan

[21] Appl. No.: 803,700

[22] Filed: Dec. 2, 1985

[30] Foreign Application Priority Data

Dec. 5, 1984 [JP] Japan ................. 59-257118

[51] Int. Cl.$^4$ ............................................. C07C 63/64
[52] U.S. Cl. ..................................... 562/495; 560/104; 526/285
[58] Field of Search ........... 562/495; 560/104
[56] References Cited

U.S. PATENT DOCUMENTS

| | | | |
|---|---|---|---|
| 3,501,297 | 3/1970 | Cremeans | 430/374 |
| 3,999,946 | 12/1976 | Patel et al. | 23/253 |
| 4,189,399 | 2/1980 | Patel | 252/408 |
| 4,562,141 | 12/1985 | Tieke et al. | 526/285 |

FOREIGN PATENT DOCUMENTS

| | | | |
|---|---|---|---|
| 1695 | 7/1981 | European Pat. Off. | 526/285 |
| 143308 | 4/1982 | Japan | 526/285 |

OTHER PUBLICATIONS

Himbert, G. et al., Z. Naturforsch, B: Anorg. Chem. Org. Chem., 39B(5), 661–667, 1984.
Gough, S.T.D., J. Chem. Soc., 1964 (Jan.), 543–544.
G. Eglinton and W. McCrae, Advances in Organic Chemistry, vol. 4, 225, (1962).
B. Tieke and G. Lieser, J. Colloid Interface Sci., vol. 88, No. 2, 471, (1982).

*Primary Examiner*—Paul J. Killos
*Attorney, Agent, or Firm*—Armstrong, Nikaido, Marmelstein & Kubovcik

[57] ABSTRACT

Amphiphilic diacetylene compound having benzene ring. The compound can readily form a single crystal and is photopolymerizable. A stable monomolecular film or built-up film can be prepared from the diacetylene compound. The film is useful as various electronic materials and optoelectronic materials.

2 Claims, 4 Drawing Sheets

AMPHIPHILIC DIACETYLENE COMPOUND CONTAINING BENZENE RING AND FILM PREPARED THEREFROM

BACKGROUND OF THE INVENTION

The present invention relates to a novel amphiphilic diacetylene compound having both of a hydrophilic group and a hydrophobic group, and also relates to a film prepared therefrom.

Heretofore, there are known symmetric diacetylene compounds of the formula:

$$R-C\equiv C-C\equiv C-R$$

wherein R is carboxyl group or an organic group having an ester group, a sulfonate group, urethane bond or hydroxyl group, as described in U.S. Pat. Nos. 3,501,308 and 4,384,980. In U.S. Pat. No. 3,501,297, there are disclosed symmetric diacetylene compounds having carboxyl groups or groups containing an ester group at both ends and having at least two methylene groups which bond the end groups to the diacetylene.

On the other hand, as asymmetic diacetylene compounds, there are disclosed in U.S. Pat. No. 3,501,297 compounds having carboxyl group and benzene ring. In the asymmetric diacetylene compounds, however, the diacetylene bond and the benzene ring or the carboxyl group are not directly conjugated and an ester bond is between the diacetylene and the benzene ring.

A stable monomolecular film cannot be prepared even if a solution of the symmetric diacetylene compound (disclosed in U.S. Pat. No. 4,384,980) or the diacetylene compound having carboxyl group (disclosed in U.S. Pat. No. 3,501,297) in a proper solvent such as chloroform, n-hexane or benzene is spreaded on water surface, because the compound does not have a hydrophobic molecular structure of an appropriate length. Further, the compounds cannot provide a built-up film (L-B film) by means of Langmuir-Blodgett method.

In addition, there are facts that the linear diacetylene compounds redily form a single crystal and that the compounds can be polymerized in solid state with ultraviolet rays, γ-rays, heat and the like. Also, multilayered thin films such as L-B films can be photopolymerized [G. Lieser, B. Tieke and G. Wegner, Thin Solid Films, 68, 77(1980)].

Heretofore, there has not been known as asymmetric diacetylene compound having both of carboxyl group and benzene ring which are conjugated with the diacetylene group. Accordingly, there has not been known, of course, a monomolecular film or a built-up film prepared from such a compound.

An object of the present invention is to provide an amphiphilic diacetylene compound which has a hydrophilic molecular structure such as carboxyl group or hydroxyl group, benzene ring and an hydrophobic molecular structure such as a chain having an appropriate amount of methylene groups, and has properties of conjugated triple bond.

Another objects of the present invention is to provide a monomolecular film and a built-up film prepared by using the amphiphilic diacetylene compound.

SUMMARY OF THE INVENTION

According to the present invention, there can be provided an amphiphilic diacetylene compound containing benzene ring of the formula (I):

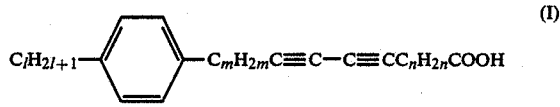

wherein "l", "m" and "n" $\geq 0$, $8 \leq l+m+n \leq 25$; and a film prepared from the amphiphilic diacetylene compound containing benzene ring of the formula (I).

The compound (I) can form a monomolecular film and a built-up film, and in the film the compound can redily form a single crystal like the linear diacetylene compounds mentioned above. Further, the compound (I) can be polymerized in solid state with ultraviolet rays, γ-rays, electron beams, heat and the like, and also the multilayered thin film such as L-B films can be photopolymerized.

The compound and the film of the present invention can be used as electronic materials such as photoconductive materials and photo and eB resist materials, optical devices such as photo-responsive materials and nonlinear optical materials, and the like.

DETAILED DESCRIPTION

Figure 1:
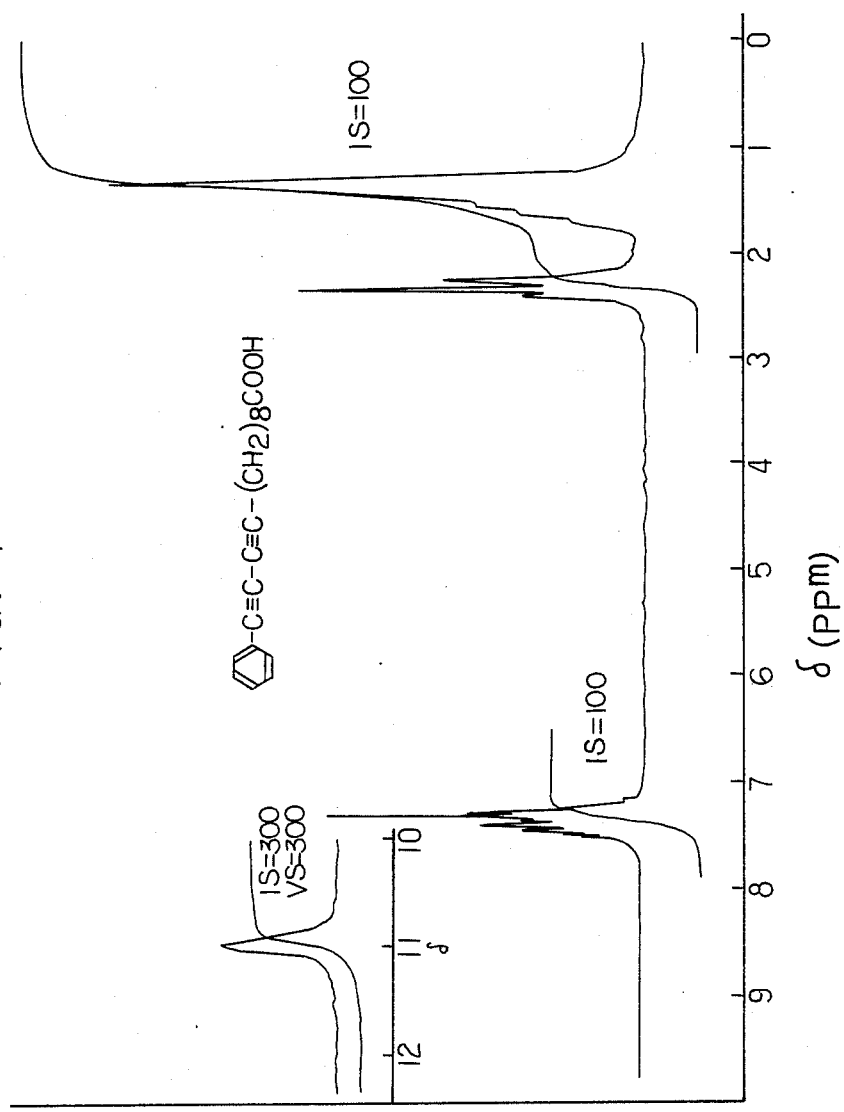
FIG. 1 and FIG. 2 are a $^1$H NMR spectrum chart and IR spectrum chart of 13-phenyl-10,12-tridecadiynoic acid prepared in Example 1, respectively.

The amphiphilic diacetylene compound of the present invention is a novel compound having the formula (I):

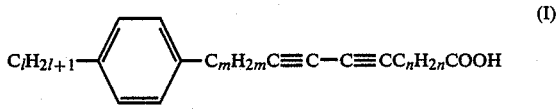

wherein "l", "m" and "n" $\geq 0$ and $25 \geq l+m+n \geq 8$.

The compound has a hydrophilic COOH group and a hydrophobic

group and $-C_nH_{2n}-$ group in the molecule, and thus shows amphiphilic property. Therefore, a monomolecular film and a built-up film can readily be prepared from the compound (I) by a usual manner. Further, since the compound has the $-C\equiv C-C\equiv C-$ group in the molecule, 1,4-addition reaction occurs. For instance, when an L-B film is prepared from the compound (I) and the 1,4-addition reaction is conducted by means of photopolymerization method, a strong film having π conjugation bond can be obtained.

In the formula (I), each of "l", "m" and "n" is 0 or a positive integer and l+m+n must be not less than 8 and not more than 25. When l+m+n is less than 8 a stable monomolecular film cannot be formed on water surface because percentage of the hydrophilic group is larger than that of the hydrophobic group, and thus the compound is partially dissolved in water. When l+m+n is more than 25, a stable monomolecular film cannot be also formed on water surface as in case of being less than 8 because percentage of the hydrophobic group becomes too large. Particularly when "m" and "n" are 0, since the benzene ring and the carboxyl group bond directly to the diacetylene structure, a conjugation system is formed. In this case where the compound has a wide π-electron system, the compound is usable as electronic materials and optoelectronic materials.

In the following, embodiments of a process for preparing the compound (I) of the present invention are explained.

The diacetylene compound of the invention can be prepared, for instance, by means of a method where two acetylene compounds are coupled.

Namely, one of the acetylene compounds is dissolved in a solvent and adding copper chloride as a catalyst to prepare a solution of copper acetylide. The solvent must dissolve the copper acetylide. Non-restrictive examples of the solvent are, for instance, water, methanol, N-methylpyrrolidone.

The other acetylene compound is dissolved in a proper solvent after converting the end—CH to—CBr by using an aqueous solution of NaOBr or the like. The coupling reaction is carried out, for instance, by adding dropwise the latter solution to the former copper acetylide solution.

The reaction conditions such as a reaction temperature, may be selected depending on the kinds of the used copper acetylide solution and the Br-modified acetylene compound. In general, the reaction is conducted at a room temperature by using copper chloride as a catalyst in an amount of about 1% by mole on the basis of the starting acetylene compound. The yield is about 40 to 70%.

The obtained compound (I) is amphiphilic. By utilizing the amphiphilic property, a monomolecular film can be prepared by preparing a dilute solution (concentration: $10^{-3}$ mole/l) of the compound (I) in a solvent which has a high vapor pressure and is insoluble in water, such as chloroform, benzene or hexane, falling gently the solution dropwise on a sufficiently wide and clean water surface, evaporating the solvent, and reducing the effective area of the compound spreaded on water surface.

When preparing the monomolecular film and repeating the Langmuir-Blodgett method, a built-up film having layers of the desired number, preferably 1 to 500 can be obtained, which are two-dimensionally arrayed in a regular manner. The thickness of the built-up film is, in general, about 20 to 15000 Å. The conjugated diacetylene portion is polymerized with electron beams, ultraviolet rays, γ-rays or heat to produce an ultrathin polymer film which has a highly ordered molecular configuration.

According to the process mentioned above, highly functional polymer films having a highly ordered structure can be prepared.

The monomolecular film and the built-up film thus obtained are useful as an organic ultrathin layer for electronic materials such as electroconductive materials and photoconductive materials. Also, the films can be used as resist materials being polymerizable with γ-rays, electron beams and the like. Further, it is possible to use the films for optical waveguides because the organic ultrathin film has an ordered configuration. Moreover, the films can be used as materials for integrated optical circuits because the films are high nonlinear optical property.

A startified organic ultrathin film may be prepared by using the diacetylene compound (I) alone, and may be prepared by admixing the compound (I) with other organic compounds. Examples of the other organic compound are, for instance, suturated fatty acids such as stearic acid and a compound of the formula: $C_lH_{2l+1}-C\equiv C-C\equiv CC_mH_{2m}COOH$ (wherein "l" and "m" are as defined above); carboxylic acids having a double bond or triple bond at ω position such as a compound of the formula: $H_2C=CHC_kH_{2k}COOH$ (wherein "k" is an integer of 8 to 25) and a compound of the formula: $HC\equiv CC_kH_{2k}COOH$ (wherein "k" is as defined above), and the like. The film prepared by using the mixture can also be useful as the materials mentioned above, e.g. electronic materials and optoelectronic materials.

In case of preparing a monomlecular film or a built-up film by using the mixture of the diacetylene compound and the fatty acid, the linear diacetylene compound or the carboxylic acid having a double bond or triple bond at ω position, the mixing ratio thereof is not particularly limited. Preferably, the other compound is used in an amount of 0.25 to 4 moles per one mole of the diacetylene compound (I). Within the range the properties of the diacetylene compound (I), particularly photopolymerizability is not reduced. When the amount of the other compound is larger than that amount, the photopolymerizability becomes low.

In this case, it is preferable that "n" in the formula (I) and "k" in the formula: $H_2C=CHC_kH_{2k}COOH$ or the formula: $HC\equiv CC_kH_{2k}COOH$ are same, because the diacetylene group in the compound (I) and the unsaturated group in the other compound are located at approximately the same position in the film, and thus polymerization easily occurs between the compounds.

The present invention is more specifically described and explained by means of the following Examples. It is to be understood that the present invention is not limited to the Examples, and various changes and modifications may be made in the invention without departing from the spirit and scope thereof.

EXAMPLE 1

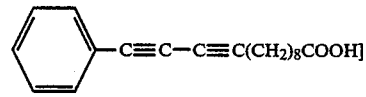

A four neck flask was charged with 10 ml of N-methylpyrrolidone, and 1.02 g (10 mM) of phenylacetylene was dissolved therein. Separately one dropping funnel was charged with 150 mg of hydroxylamine hydrochloride, 100 mg of copper chloride and 5 g of a 70% aqueous solution of ethylamine, and another dropping funnel was charge with 2.61 g (10 mM) of 11-bromo-10-undecynoic acid in 10 ml of a 10 % methanol solution of potassium hydroxide. After attaching the funnels to the flask, the flask was filled with nitrogen gas and then the mixture was kept at 15° C. First the ethylamine solution of copper chloride was added dropwise while vigorously agitating the mixture in the flask. Then the methanol solution of potassium hydroxide which dissolved 11-bromo-10-undecynoic acid was added dropwise for 1 hour at 20° C. while agitating the mixture. The agitation was continued for another 6 hours at 20° C. While keeping the inner temperature of the vessel at a temperature of not more than 22° C., 2N-aqueous sulfuric acid solution was added dropwise to change the reaction mixture from alkaline state to acid state. After adding 100 ml of water, the mixture was extructed with 500 ml of diethyl ether. The obtained ether layer was dried on anhydrous sodium sulfate, followd by removing the ether. The residue was recrystallized from petroleum ether to give a crystal of 13-phenyl-10,12-tridecadiynoic acid (yield: 48%).

Figure 2:
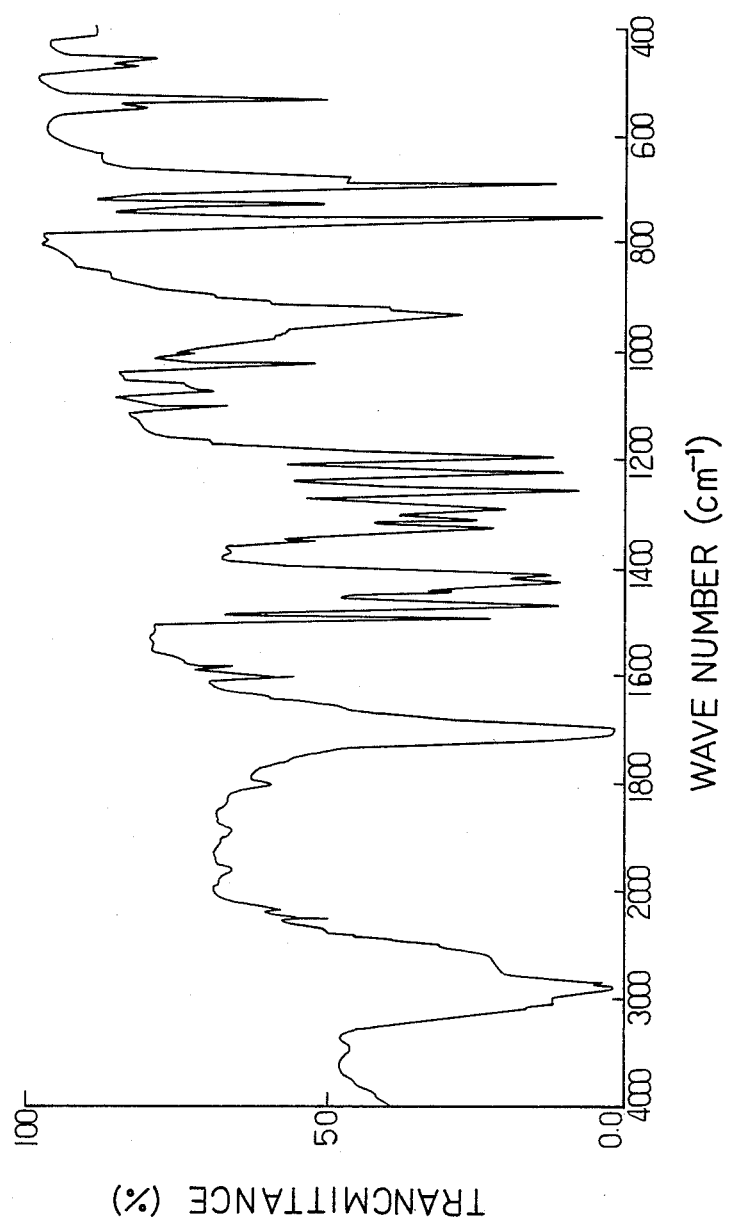

The thus obtained 13-phenyl-10,12-tridecadiynoic acid has a melting point of 82.° to 83° C. As a result of $^1$H-NMR spectro-analysis and IR spectro-analysis, the structure of the compound was identified. The results are shown in FIG. 1 and FIG. 2.

The $^1$H-NMR spectro-analysis was conducted under the condition, i.e. in CDCl$_3$, with a pulse having 20 $\mu$ sec width and at integrating number of 100. In FIG. 1, IS menas a read intensity of integrated value, and VS means a read intensity of spectral peak. The IR spectroanalysis was conducted by means of KBr method by scanning over all wave lengths for 6 minutes.

EXAMPLE 2

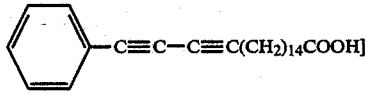

A mixture of 16-heptadecynoic acid and 19- phenyl-16,18-monadecynoic acid (4:1, molar ratio) was dissolved in chloroform to prepare a solution having a concentration of $10^{-3}$ mole/l.

Separately, CdCl$_2$ and KHCO$_3$ were added to water which was distilled twice so that the concentration thereof were $3 \times 10^{-4}$ mole/l and $5 \times 10^{-5}$ mole/l, respectively. Onto the surface of the water having an area of 562.5 cm$^2$, 103.681 $\mu$l of the solution prepared above was dropped, and then the formed film was compressed by moving a barrier at a constant moving rate of 5 Å$^2$/min. The changes of surface area of the film and surface pressure were measured at 15° C. with an apparatus of MGW LAUDA available from Messgeräte-Werk LAUDA Dr. Wobser KG.

Figure 3:
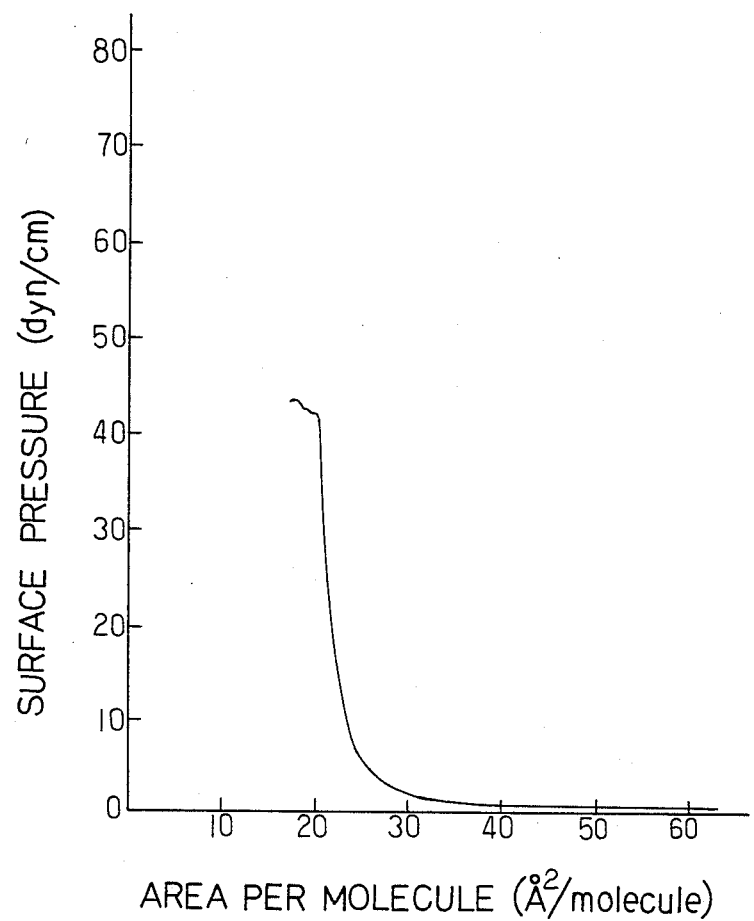
FIG. 3 is a graph showing a relation between an area per molecule and a surface pressure measured in Example 2.

The results are shown in FIG. 3. In FIG. 3, the oxdinate means an area per molecule and the abscissa means a surface pressure.

As is clear from FIG. 3, the surface pressure was drastically raised near 30 Å$^2$/molecule, which shows the formation of a monomolecular film.

The above solution of the diacetylene comound was dropped onto the surface of the water at 15° C., and then a monomolecular film was formed by applying a constant pressure of 25 dyn/cm. After 30 minutes from the dropping, a quartz plate which was subjected to hydrophobic surface treatment with cadmium arachidate was reciprocally moved in the perpendicular direction to the water surface to prepare a built-up film of 14 layers on each side of the quartz plate.

Figure 4:
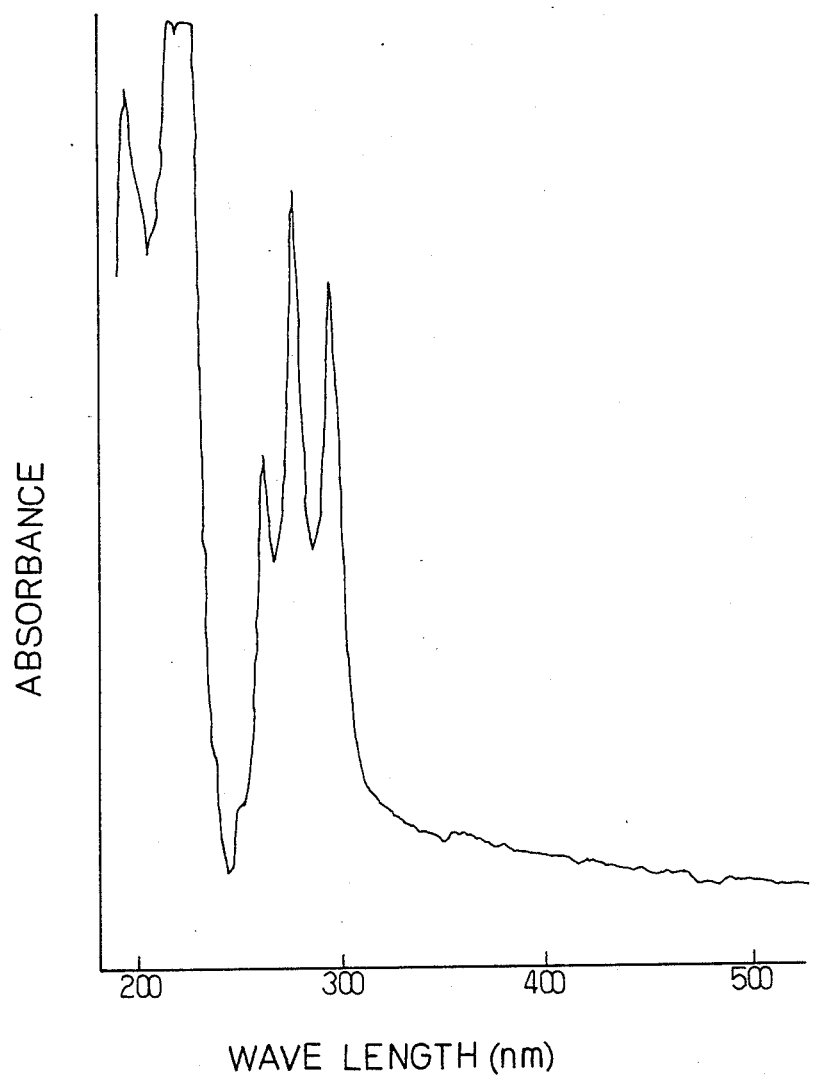
FIG. 4 is a UV spectrum chart of the built-up film prepared in Example 2.

The obtained built-up film was analyzed by means of UV spectro-analysis. The results are shown in FIG. 4. The UV spectro-analysis was carried out over visible ray range and ultraviolet ray range for 12 minutes.

As is clear from FIG. 4, the film has three peaks of the absorption of the diacetylene which was conjugated with the phenyl group.

In addition to the ingredients used in the Examples, other ingredients can be used in the Examples as set forth in the specification to obtain substantially the same results.

The compound (I) of the present invention has, as mentioned above, various excellent properties and effects. For example, since the compound (I) has the benzene ring, the diacetylene ring, the hydrophobic group of a proper length and the hydrophilic group, a stable monomolecular film can be prepared by dissolving the compound (I) in a solvent such as chloroform or benzene and spreading the solution on water surface. Accordingly, a multilayered built-up film can be easily prepared by moving a plate such as a quartz plate or a metal plate up and down. Further, when the distance between the diacetylene group and the benzene ring in the formula (I) is selected so that "m" is 0, an L-B film which contains benzene ring conjugated with the diacetylene group can be prepared.

What is claimed is:

1. An amphiphilic diacetylene compound having benzene ring of the formula (I):

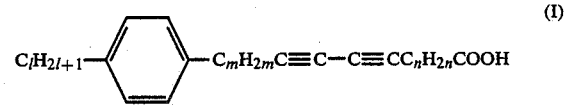

wherein "l", "m" and "n" $\geq$ 0, $8 \leq l+m+n \leq 25$;

2. The compound of claim 1, wherein "m" is 0 or "n" is 0.

* * * * *

UNITED STATES PATENT AND TRADEMARK OFFICE
CERTIFICATE OF CORRECTION

PATENT NO. :   4,748,273

DATED      :   May 31, 1988

INVENTOR(S):   Kiyoshige FUKUDA et al

It is certified that error appears in the above-identified patent and that said Letters Patent is hereby corrected as shown below:

Column 3, line 49, "10-3 mole/l" should read --$10^{-3}$ mole/l--.

Column 6, line 51 "wherein "l"," should read --wherein "$\ell$",--.

Signed and Sealed this

Fifteenth Day of November, 1988

Attest:

DONALD J. QUIGG

*Attesting Officer*      *Commissioner of Patents and Trademarks*